United States Patent [19]

Vriend

[11] Patent Number: 5,984,872
[45] Date of Patent: Nov. 16, 1999

[54] AREA AND SHAPE OF THE FLOW-VOLUME CURVE IN LUNG DIAGNOSTICS

[75] Inventor: Willem Hendrik Vriend, Brisbane, Australia

[73] Assignee: W. H. Vriend, Brisbane, Australia

[21] Appl. No.: 08/987,922

[22] Filed: Jul. 14, 1997

[51] Int. Cl.$^6$ .................................................. A61N 5/00
[52] U.S. Cl. ........................................ 600/529; 600/538
[58] Field of Search ............................................. 600/529

[56] References Cited

U.S. PATENT DOCUMENTS

| | | | |
|---|---|---|---|
| 642,149 | 1/1900 | McKenzie | 128/728 |
| 3,420,225 | 1/1969 | Holden et al. | 128/728 |
| 3,533,398 | 10/1970 | Jones | 128/728 |
| 3,889,660 | 6/1975 | Kitrilakis | 128/728 |
| 4,296,756 | 10/1981 | Dunning et al. | 128/716 |
| 4,296,758 | 10/1981 | Garbe | 128/732 |
| 4,470,429 | 9/1984 | Johnson | 137/625.46 |
| 4,635,647 | 1/1987 | Choksi | 128/725 |
| 4,736,750 | 4/1988 | Valdespino et al. | 128/728 |
| 5,190,077 | 3/1993 | Pawelski et al. | 137/625.46 |

OTHER PUBLICATIONS

Vriend, Smoky Fires,Part 2,the chronic airflow limitations of the Highlanders of Irian Jaya.

Vriend, MacLung v.1.0, Computer program,Copyright US Copyright Office May 30, 1995 (receipt 100882).

*Primary Examiner*—Robert L. Nasser
*Assistant Examiner*—Michael Astorino

[57] ABSTRACT

A spirometer set-up with an analogue to digital converter to a computer chain which allows the use of the merit function of the flow-volume curve for the discrimination between healthy persons and those who have a mechanical pulmonary function disorder, and the exact area under the flow-volume curve of lung mechanics to follow the progression of said lung disorder.

3 Claims, 5 Drawing Sheets

AREA AND SHAPE OF THE FLOW-VOLUME CURVE IN LUNG DIAGNOSTICS

CROSS-REFERENCES TO RELATED APPLICATIONS (a) TITLE OF THE INVENTION.
Area and shape of the flow-volume curve in lung diagnostics.
(b) CROSS-REFERENCES TO RELATED APPLICATIONS.
U.S. Pat. Documents

| | | | |
|---|---|---|---|
| 4,296,756 | 10/1981 | Dunning et al | 128/716 |
| 4,796,639 | 1/1984 | Snow et al | 128/725 |
| 5,320,108 | 6/1994 | Cloutier | 128/716 |
| 5,357,975 | 10/1994 | Kraemer et al | 128/725 |
| 5,277,196 | 1/1994 | Hankinson et al | 128/725 |
| 2,999,495 | 9/1961 | Shipley | 128/728 |
| 4,931,044 | 6/1990 | Beiter | 251/149.5 |
| 5,004,013 | 3/1991 | Beaston | 251/149.5 |
| 3,889,672 | 6/1975 | Woldring | 128/728 |
| 3,363,260 | 1/1968 | Garbe | 128/728 |
| 4,635,647 | 1/1987 | Choksi | 128/725 |
| 3,889,660 | 6/1975 | Kitrilakis | 128/728 |
| 3,533,398 | 10/1970 | Jones | 128/728 |
| 4,736,750 | 4/1988 | Valdespino et al | 128/728 |
| 3,420,225 | 1/1969 | Holden et al | 128/728 |
| 642,149 | 1/1900 | McKenzie | 125/728 |
| 5,190,077 | 3/1993 | Pawelski et al | 137/625.46 |
| 4,470,429 | 9/1984 | Johnson | 137/625.46 |
| 4,296,758 | 10/1981 | Garbe | 128/732 |

Publications

1. Vermaak J. C., Bunn A. D., deKock M. A.;
The area under the Maximum Expiratory Flow-Volume Curve. Respiration 37:61–65(1979)
2. William H. Press, Brian P. Flannery, Saul A. Teukolsky, William T. Vetterling;
Numeral Recipes in Pascal, The Art of Scientific Computing, 14.4 The modeling of Data in Nonlinear Models, page 572–579, Cambridge University Press, ISBN 0-521-37516-9.
3. A. J. Woolcock, K. Yan, C. Salome;
Methods for assessing bronchial reactivity, Eur J Respir Dis 1983; 64: 181–194.
4. W. H. Vriend;
Part 2 of Smoky Fires, The chronic airflow limiations of the Highlanders of Irian Jays (not yet published).
5. W. H. Vriend, MacLung© v. 1.0,
Computer program used to calculate the conventional and newly invented mechanical lung function indices; a Certificate of registration has been issued for this work under the seal of the Copyright Office in accordance with title 17, United States Code, on May 30, 1995 (receipt no. 100882, Form Txu 697–680)

STATEMENT REGARDING FEDERALLY SPONSORED RESEARCH OR DEVELOPMENT

Not Applicable.

REFERENCE TO A "MICROFICHE APPENDIX" (SEE 37 CFR 1.96)

Not Applicable.

BACKGROUND OF THE INVENTION

1. Field of the Invention

The invention relates to spirometers that are electrically connected to a computer through an analogue to digital converter. From the digital values every 10 milliseconds collected software calculates all the successive flow and volume values of a breathing exercise and graphically presents conventional mechanical lung functions and the related flow-volume curve, while it more particularly permutes the parameters that determine the shape of the flow-volume curve. To compute comprehensive new lung indices the figure-of-merit function of the maximum expiratory flow-volume curve, subsequently called the merit function, is developed to make quantitation of both the area under and the shape of that curve feasible. The calculated exact maximum expiratory flow-volume area under that curve, subsequently called the FV area, portrays the amount of oxygen that a person can collect. Indices developed from coefficients and exponents of the merit or the flow-volume's essential mathematical function make the hitherto impossible quantisation of the shape of the flow-volume curve workable.

Evaluation of old mechanical lung indices up to now used in pulmonary diagnostics, was complicated and not exact. Their values also differentiate poorly between distinctive lung function disorders and between lung patients and healthy people. The for the invention designed comprehensive mechanical lung indices open complete new perspectives in lung diagnostics.

2. Description of the Related Art Including Information Disclosed Under 374 CRF 1.97 and 1.98

Conventionally, in epidemiological research of lung diseases and diagnostic evaluation of patients, the forced expiratory flow-volume curve obtained by a forced breathing manoeuvre is widely used. Related lung indices, representing single points on that curve, may show flow limitation, the curve shape was visually used in the decision making process. The older lung indices do not take into account that the whole FV area represents the labor the thorax and lungs are able to achieve.

Conventional lung indices, like the forced vital capacity (FVC), the one second volume (FEV1), the FEV1/FVC ratio, the maximum mid expiratory flow rate (MMEFR), the peak flow rate (PEF or MEFR) and the average flow between two fixed volume percentages (FEF25–75%VC etc.) take into consideration only one or two points on the flow-volume curve.

They require complex pulmonary diagnostic systems, as presented by Dunning et al U.S. Pat. No. 4,296,756 and Snow et al U.S. Pat. No. 4,796,639. These diagnostic systems use several parameters and still do not differentiate successfully. The discriminant analysis of lung indices does not make a significant difference between those with severe symptoms and the relative healthy people. Only when we take the whole area under the flow-volume curve into account do these separation of the distribution curves becomes complete, as shown in the compilation of the Irian Jaya survey (see document 3).

Vermaak and others (see publication 1), used the area of a triangle in the flow-volume curve. The triangle is situated between the origin, the point of maximum volume and the point of maximum flow. To get an estimate of the area under the flow-volume curve the triangle was multiplied with an experimentally found average coefficient. The calculation of this area, however, did not use all the estimable points on the curves. The incorporation of an experimentally average coefficient, makes the calculation conditional to gender and anthropological differences, and neglect individual or disease related alterations. An area was also used for the mean transit time (MTT) because the area under a volume-time curve divided by the volume expired, gives the mean time it takes to expire. Some improvement in the discriminant analysis with conventional mechanical lung indices emerges. Calculating different areas of the curve (FIG. 7), namely after point zero, the point of reflection, and the one-second time point, gives the mean transit time of different parts of the volume-time curve (MTTN, MTTF, MTT1 respectively). The calculation gives an average time, depends only partially on the shape of the curve and gives no indication of the labor carried out to supply oxygen.

It is therefore an object of the present invention to provide the means to calculate the area under the flow-volume curve, by utilising all the digital values collected from the individual under investigation. The result is the maximum expiratory flow-volume area (MEFVA) in squares liters per second ($l^2$/sec). It is an exact measurement of a person's oxygen supply capacity, and is independent of the shape of the curve. It takes into account all estimable points on the curve, sampled every one hundredth of a second.

It is further an objective of the present invention, to qualify the shape of the flow-volume curve, which depend on its merit function; the function that measures the agreement between the data and the model with a particular choice of parameters.

With the merit function developed by the inventor we can model the data. However, collection of data never occurs without measurement errors. Calculations, therefore, can not be carried out with mathematical precision but have to be tested for their goodness-of-fit. As the merit function turned out to be nonlinear, we used the Levenberg-Marquardt iterative minimisation method, as described in publication 2 from Cambridge University Press 1989. The numerical calculation makes it possible to calculate the two coefficients and four exponents of the function.

The final chi-square of the numerical calculations (with this kind of function) must be lower than the number of equations minus the number of parameters (six). A chi-square, just above the norm, can still be acceptable, if the curve from the calculated formula as shown in the graphical presentation covers or fits the measured flow-volume curve. When measurement errors are not normally distributed, and inequalities are inappropriately high, but the curves cover nicely, we can still use the results. So far the parameters of the merit function have nor been used as a diagnostic tool to quantitate the shape of the flow-volume curves.

The inventor used a dry spirometer with a hinge pivoting through a vertical line, further on called the spirometer with a vertical hinge. The spirometer electronically samples digital values every hundredth of a second. The digital values are stored in an array, and represent changes in volume during the breathing exercise. The software calculates a calibration factor from the digital values before, and after, injection of two liters of air into the spirometer. Temperature and altitude readings are incorporated into the data. Flow and volume values are estimated, from this data, using a calibration factor and a body-temperature pressure-saturated (BTPS) correction factor, selected from a data base.

It would be possible to connect a 'Portable Flow-Type Spirometer With Improved Accuracy' as disclosed by Hankinson et al. U.S. Pat. No. 5,277,196, instead of the dry spirometer used. Such a flow-type spirometer was not used in conjunction with the invention. It though would have made the outfit smaller but was not available by the time of the survey (1998–92). The Hankinson is more accurate than the earlier hot-wire flow-type spirometric systems that showed nonlinearity and a sensor drift.

The volume-type spirometer used in the survey maintains linearity by the arcing movements of the moving panel point being referred to a potentiometer. There is no zero drift because bellow movements begin at a start block. Hankinson claims that the updated flow-type spirometer is also linear and has no zero-drift. Consequently the systems are compatible, except for the volume which will need to be calculated from the flow values. Mobility and hardness of the flow-volume device as disclosed by Kraemer and others in U.S. Pat. No. 5,357,975, however, works at the expense of manually iterated measurements to shape a flow-volume curve. The shape, which is so important in diagnostics, deteriorates into a triangle without any guarantee that the area reflects the oxygen supply capacity.

The invention which uses a merit function of a flow-volume curve can be used, in epidemiological surveys as well as for clinical and doctor practices, and no remote controls, like in the Dunning' Remote Pulmonary Function Tester, are required. It also opens the way to supermarked self-control as done with blood pressure and cholesterol level monitors. The MEFVA gives a good qualitative prognosis of the momentary oxygen supply capacity and shows its change over time. The undimentional values from the coefficient proportionality index (CFI) and exponent proportionality indices (HPI-1 and 2), as described later, have a sharp boundary. This makes lung diagnostics much like a blood sugar level estimate in diabetes. For an explanation refer 'Detailed Description of the Invention' under section h.

For clinical use in diagnosis of lung disorders and evaluation of treatment, other functions, like diffusing capacity, residual volume, resistance, alveolar volume and blood gasses, can be better judged when the supply side is defined accurately. In improved bronchial provocation tests as invented by Cloutier (U.S. Pat. No. 5,320,108) for occupational asthma, or in bronchial reactivity studies, in the clinic and by population studies (Woolcock in publication 3), the MEFVA would be of great help.

The vertical hinge of the spirometer manufactured to collect data for the investigation, obliterates the gravitational pull on the bellow in the direction of the volume extension. Garbe (U.S. Pat. No. 4,296,758) and Shipley (U.S. Pat. No. 2,999,495) have a horizontal hinge. Shipley in FIG. 4 clearly shows the influence of gravidity. The bellows, or clocks, of the volume-type spirometer as used by McKenzie (U.S. Pat. No. 642,149) moving up and down, Woldring (U.S. Pat. No. 3,889,672) and Kitrilakis (U.S. Pat. No. 3,889,660) moving sidewards around a horizontal spindle, are all subjected to gravity, which hampers their volume extension. Jones (U.S. Pat. No. 3,533,398) moving sidewards does not has the gravitational pull but needs a lot of valves to direct and thus hamper the air stream. Choksi (U.S. Pat. No. 4,635,647) used a collapsible bellow and could measure only a desired range of airflow. Valdespino et al. (U.S. Pat. No. 4,736,750) used a bellow to proceed from airflow into volume measurements but could only estimate the values FVC, FEV1 and FEV1/FVC.

Holden (U.S. Pat. No. 3,420,225) used two hinges with horizontal spindles to operate under the influence of acceleration forces going toward and being in outer space, the changes in volume measured with a potentiometer. It is obvious that the invention could not have been made with the data from a lung survey in stone age times in the Highlands of Irian Jaya with advise from several universities and without funding using equipment for outer space. Potentiometer movements of the in space used Holden invention, however, are not linear as the bellows move along an arc and do not behave as a triangle (see Description of the Preferred Embodiments). Not to mention yet the hampering friction of the bellows so near to the hinge.

Linearity and independence from gravidity are important preconditions because breathing, limited or not, is a continuous movement, and the Marquardt method can only calculate a continuous function, because it depends on six partial derivatives.

A revolving valve connecting a subject or calibrator to the spirometer or to the spirometer and ambient air also contributes to a smooth, continuous registration of the breathing movement, as no moving valves hamper the airflow like in the McKenzie version. Beaston (U.S. Pat. No. 5,004,013) made a Dripless Coupling Device and Beiter (U.S. Pat. No. 4,931,044) a Blood Collection Valve for fluids. They, however, connect one channel only and would not give the possibility to connect a spirometer to the ambient air while the subject or calibrator are still connected. This is necessary to readjust the start point, to release false pressures and to refresh the interior of the bellows. The Beason valve instead retains the fluid which is already in the apparatus. Pressure release could be done by opening the mouth peace or disconnect the calibrator, but is often not practised in every day life.

Pawelzik et al. (U.S. Pat. No. 5,190,077) made a Switchover Valve and Johnson (U.S. Pat. No. 4,470,429) a three-way valve for fluids that would put the airflow of a breathing manoeuvre into turmoil because of the sharp angles and obstruction of the rotary valves. A four-way valve of this type with the requirements of an 1.5 inch input pipe diameter for a breathing manoeuvre would not match when the spirometer was connected with one of the valves. Only the long large openings like 19 in FIG. 3 make an easy going airflow possible. Eng. E. Vanuytven from Intersoft Electronics, who invented the "MacFactory™" for use with the Macintosh computer, was so kind to write me the MacScoop software program in FORTH, to interface "MacFactory™" to collect the data.

BRIEF SUMMARY OF THE INVENTION

The first objective of the invention is to provide the means for an exact estimate of the maximal amount of labor the lungs are able to provide in square liters per second. To achieve this, we must determine the exact area under the flow-volume curve (MEFVA). From digital values sampled by the spirometer, utilising an AD converter to computer chain, the software program MacLung© (document 5) calculates the area with a cartographic formula, and shows this area on the screen. The program collects the appropriate arrays and calculates the area, for rest (TFVA), and after exercise (WFVA). The program computes conventional mechanical lung functions (for comparison) and shows a graphical representation of the corresponding coordinates, radiant and other relevant lines.

The second objective of the invention, is to define the curve shape. The program, MacLung©, calculates two best-fit coefficients, $a_1$ and $a_4$, and two best-fit exponent pairs ($a_2$, $a_3$) and ($d_{5,a6}$) for the merit function that fit the respiration curve under consideration. The Marquardt method, mentioned earlier, resolves the parameters from the equations generated with the flow and volume sampled values. The coefficient proportionality index or CPI-$a_1/a_4$ and the two exponent proportionality indices EPI-1=$a_3/a_2$ and EPI-2=$a_3/a_6$ are computed from the parameters.

All three the quotients deliver an undimentional number (not expressed in units) and have a critical value, where the form changes dramatically. The critical values are 3, 4 and 4 respectively. The measured flow-volume curve and the corresponding merit function curve plotted simultaneous on the screen, make analysis of the findings simple.

To provide the means for an unhampered continuous airflow in a volume-type spirometer a revolving valve and a bellow with a vertical hinge were used. A 'Portable Flow-type Spirometer With Improved Accuracy' as disclosed by Hankinson et all. U.S. Pat. No. 5,277,196, however, would make the set-up easier to handle.

In achieving the two objectives, the diagnosis of mechanical lung function disorders is put on a comprehensive and reliable basis. To date, diagnosis and progress evaluation, depend only on a subjective evaluation of the curve shaped and on some subordinate solitary points on the flow-volume curve.

BRIEF DESCRIPTION OF THE SEVERAL VIEWS OF THE DRAWING(S)

The present invention will be more fully understood by reference to the following detailed description thereof when read in conjunction with the attached drawings and wherein.

DESCRIPTION OF THE INVENTION

Figure 1:
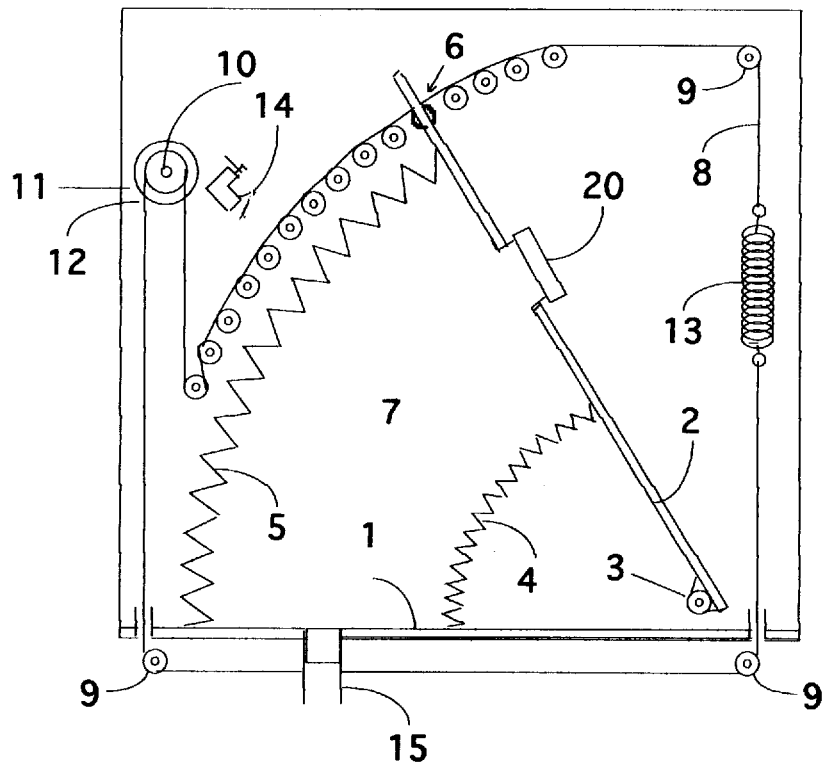
FIG. 1 is a schematic horizontal cut through the spirometer used to collect data.

As the invention depends on a correct registration of a continuous breathing curve a description therefor of the methods that enabled the discovery of the invention must follow. The influence of gravity on equipment should be minimal, airflow should be uninterrupted and bellow movements always start at the same point while the relation between digital registration and volume changes must be linear.

To make spirometer movements relatively independent of gravidity, a bellow, mounted between two rigid planes moving between them through a hinge with vertically positioned spindle, later called the vertical hinge. In the horizontal cut-through figure no 1 these are a fixed or a stationary panel (1) and a vertical panel (2) that moves. The movement of the last panel enables the bellows to contract and expand in the angle between both vertical planes. Every point on the bellow describes an arc within this angle which has its centre in the vertical hinge axis on the matching height. The vertical hinge (3) makes movements around two small ball-bearings situated at both ends with a negligible resistance. Gravity can only sag the bellows down, mostly in the middle. To keep this to a minimum the bellows are enforced with Formica busks (4, 5) on all four sides.

The volume changes of the spirometer are linearly related to the spirometer movements. To relate the changes to the spirometer a cord is attached to the moving panel with attachment brackets at fixation point 6.

The movements of the fixation point on the moving panel (2) follow an arc and are linearly related to the volume changes of the bellows (7) by the formula $V_B=\frac{3}{8} H.I..r_c^2$. Where $V_B$ is the volume, H the height of the bellow, and L the length of the arc. The radius, of the external bellow wall (5), squared ($r_c^2$) is a constant.

Figure 2:
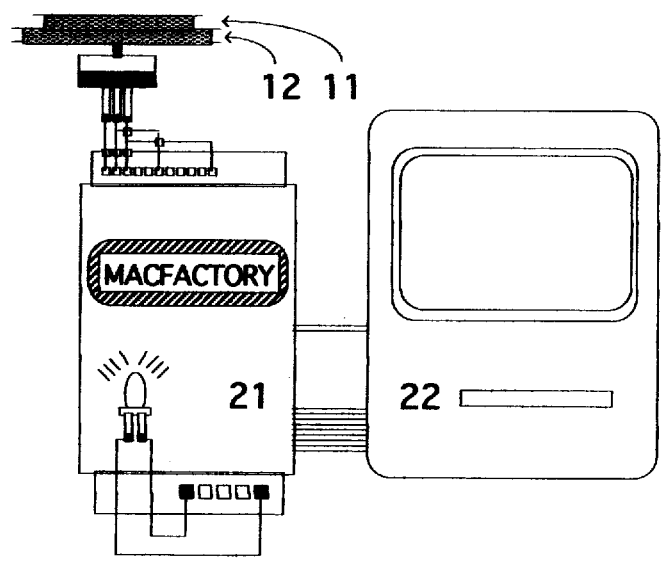
FIG. 2 is a flow chart of the computer chain.

The radius of the internal wall, $R_i$(4), is half the length of $r_c$(5) the latter being 50 cm. The height, H, is 25 cm. A nylon cord (8), runs on small ball-bearing pulleys (9) placed along the arc, on the corners of the spirometer and around a pulley wheel on the potentiometer (10) to drive the potentiometer in response to movement of the loop. The cord is fixed to point 6, the fixation point, on the moving panel (2). The potentiometer pulley, as shown in FIG. 2, has two diameters, one for adults (11) the other for children (12). A spring (13) keeps the cord from slipping around the potentiometer pulley and makes the adult to children change and it's reverse possible.

At position 14, there is a lock for the moving panel, where maximum expiration starts. This assures that after the lock is opened, the movement always starts at the same point. Plasticised canvass cloth (as used for seat covers) insures flexibility and impermeability of the bellows.

Figure 3:
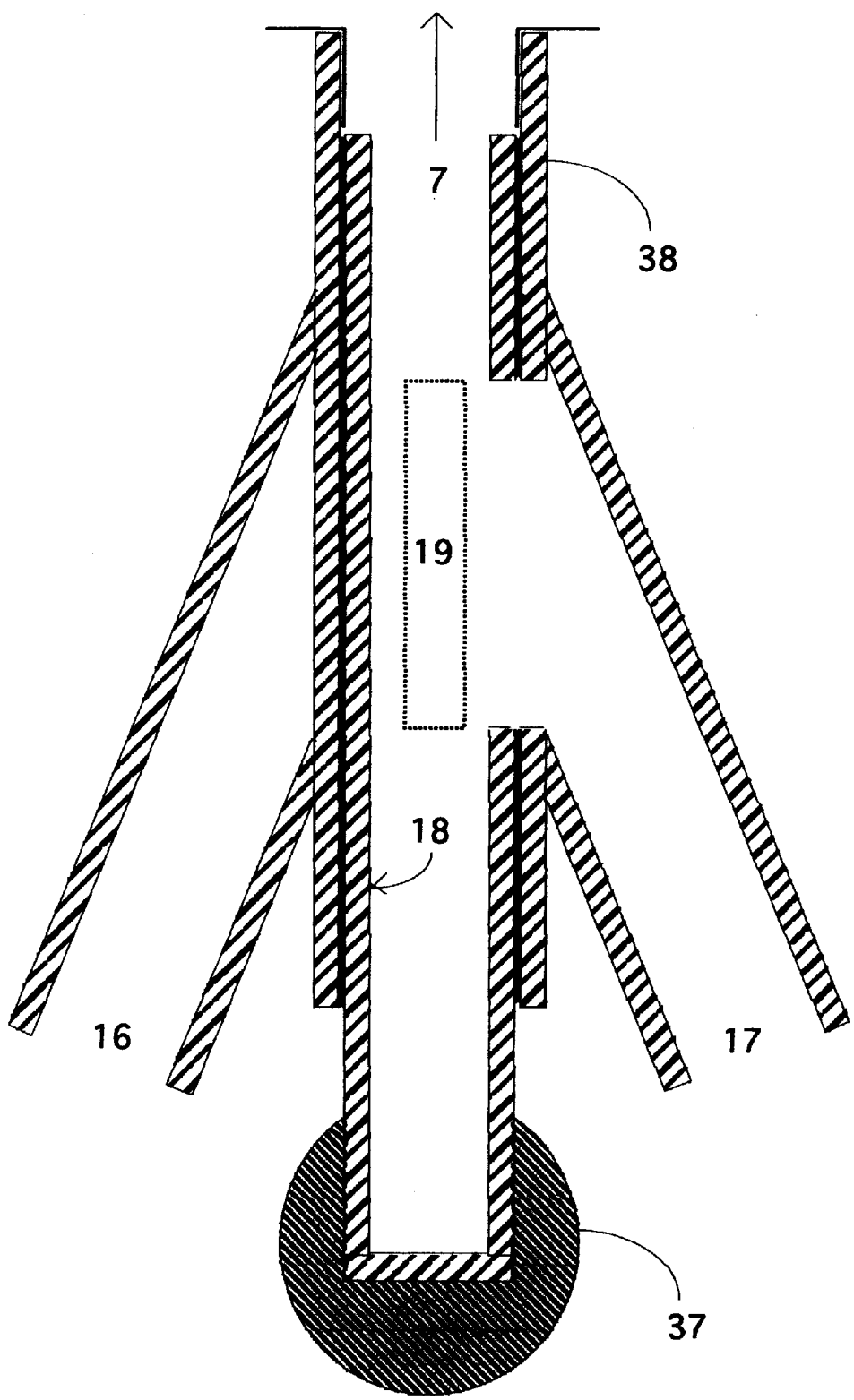
FIG. 3 is a longitudinal cut through the constructed revolving valve of the spirometer.
Figure 4:
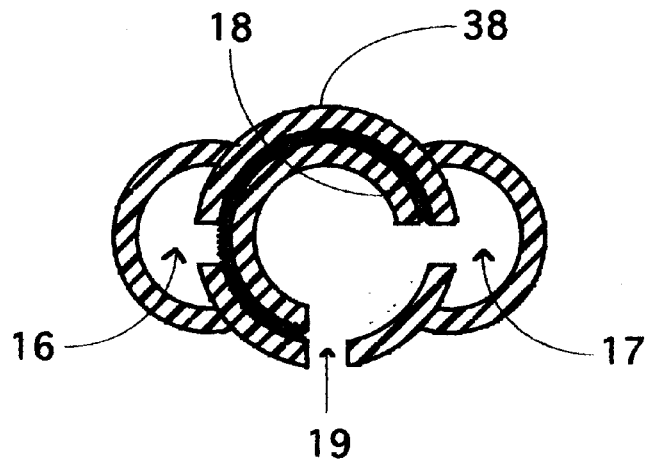
FIG. 4 is a transferral cut through the constructed revolving valve of the spirometer.

The spirometer inlet pipe (15) has a four-way revolving valve mounted on to it. The hereinafter so-called revolving valve consists of an outer (38) an inner tube (18). The tubes are sealed off against each other by a layer of felt glued on the inner tube. The outer tube closed off towards the breathing person by the inner tube which is sealed off to the outside with a knob (37). The open end of the outer tube (7 in FIG. 3) attached to the outlet of the spirometer bellows connect (as shown in FIGS. 3 and 4) to the breathing person, the inner channel (16), or to the two liter calibration syringe (17) or the room air (19) through three long rectangular openings in the inner tube each matching in size with the 1.5 inch breathing pipe. By turning the inner tube knob (18) to the two downwards positions (FIG. 3), the spirometer and the patient or calibrator also connects to the ambient air (19), the air around the spirometer. By turning the inner tube in the two upwards positions the spirometer comes into contact with the breathing person or the calibrator. Consequently the revolving valve has the possibility of making four different connections. The interior of the bellows can be accessed through a hole in the moving panel closed with a screw-cap (20).

One of the outer leads of the potentiometer (10) connects to the ground of the analogue to digital converter (21) "MacFactory™." The middle lead runs to A8 and A4, and the third potentiometer lead goes to both A7 and A10 on the AD converter. A red LED connected to B4 and ground shows when the power is switched on. For the AD converter, a 12 Volt 100 mA supply line goes to the power points on the computer board. A serial connection goes to the modem input of the Apple™ Macintosh Plus (22) that was used.

Figure 6:
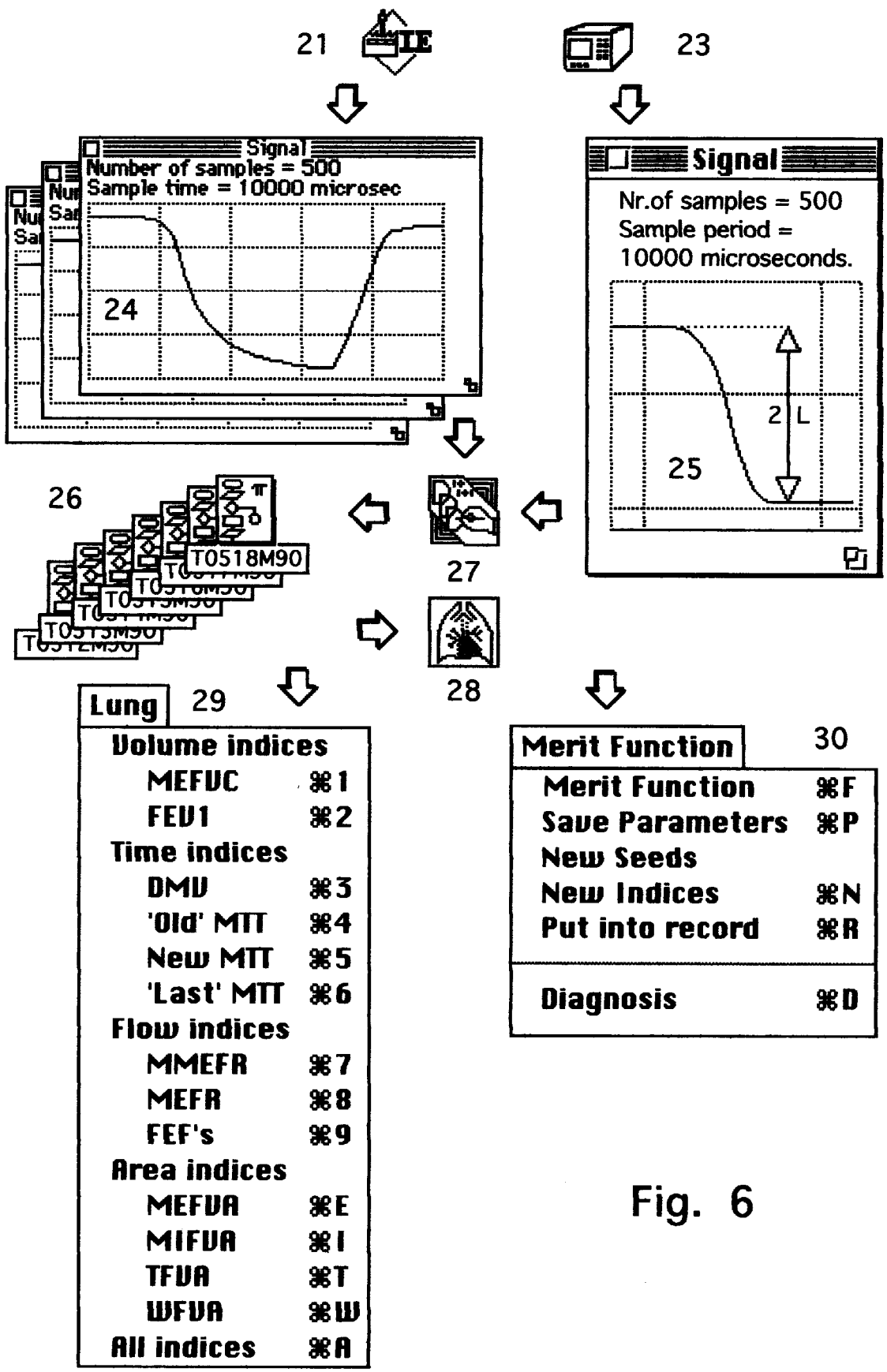
FIG. 6 is a chart with icons from programs used and developed for the invention.
Figure 7:
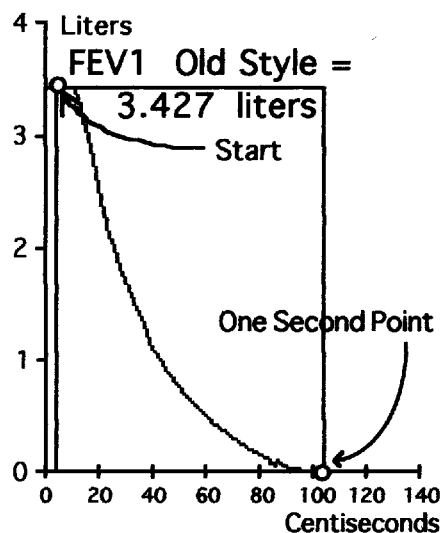
FIG. 7 is an example of the graphical presentation of the conventional mechanical lung indices with their relevant fitting lines.
Figure 7:
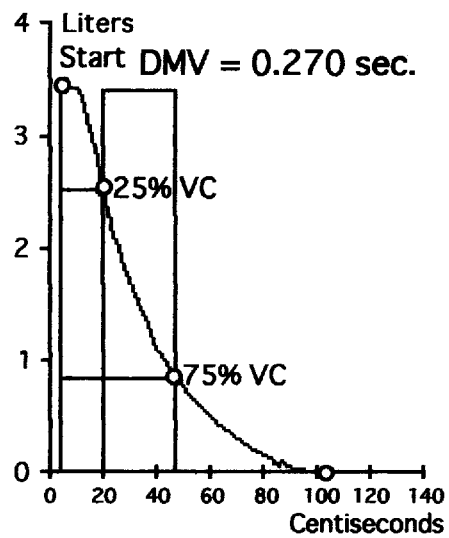
Figure 7:
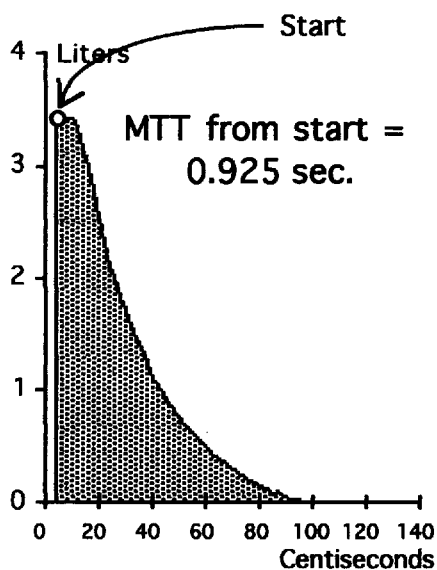
Figure 7:
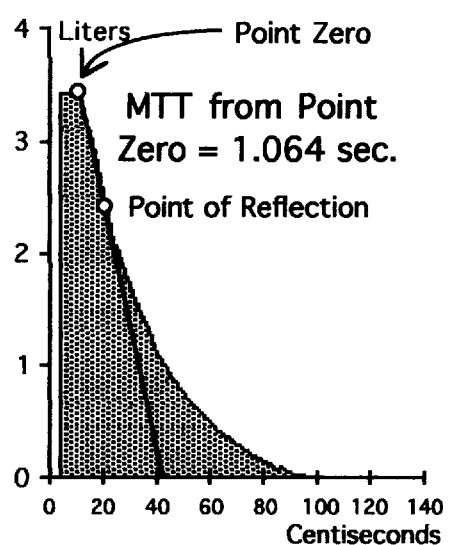
Figure 7:
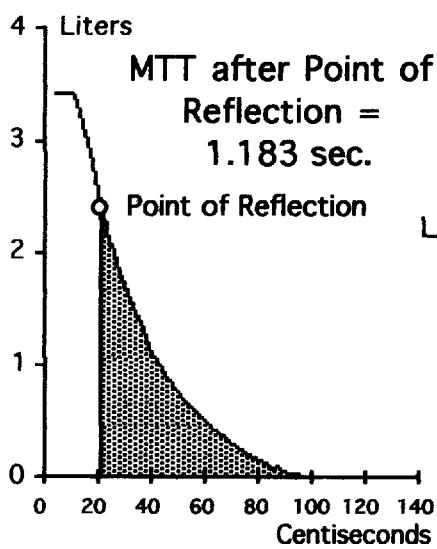
Figure 7:
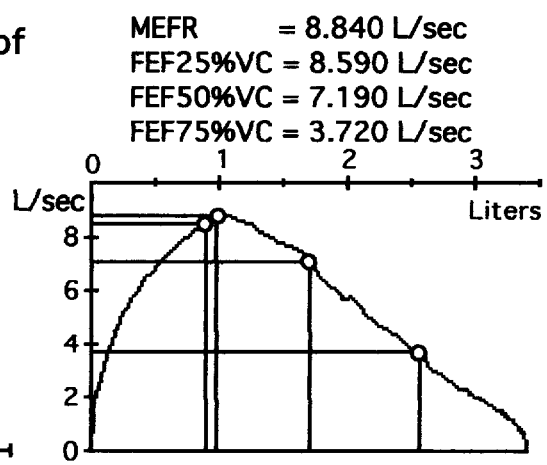

As seen in FIG. 6, the application "MacScoop" shows the immediate graphic representation (24, 25) of the potentiometer's output on the screen. It delivers a list of 500 digital readings (sampled at 10 milliseconds), on the Apple Clipboard.

A program written in MS BASIC—compiled with 3DBASIC (27)—selects the best breathing movement of the subject under investigation, from a persons' three files stored in the Scrapbook. The best performance is saved in a subject file (26) and read by the application "MacLung©" (written and compiled in THINK-PASCAL (28)).

Using the menu lung indices (29) of the "MacLung©" application, the following lung indices calculated, and graphically presented, come up on the screen. With the proper inherent lines, attached to the respective volume-time or flow-volume curve, they are:

FVC, FEV1, FEV1/FVC percentage;
MEFR and it's VC%, MMEFR and it's DMV;
FEF25%, 50% and 75%;
MTT and the newly developed MTTN and MTTF;
the new MEFVA, MIFVA, WFVA and TFVA.

To calculate the area under the flow-volume curve the program uses the following formula expressed in square liters per second:

$$ABS[\{(x_1+x_2)\cdot(y_1-y_2)+(x_2+x_3)\cdot(y_2-y_3)+\ldots +(X_n+X_{n-1})\cdot(Y_n-Y_{n+1})\}/2].$$

where n is the number of readings and $X_{n+1}=X_1$ $Y_{n+1}=Y_1$.

Figure 5:
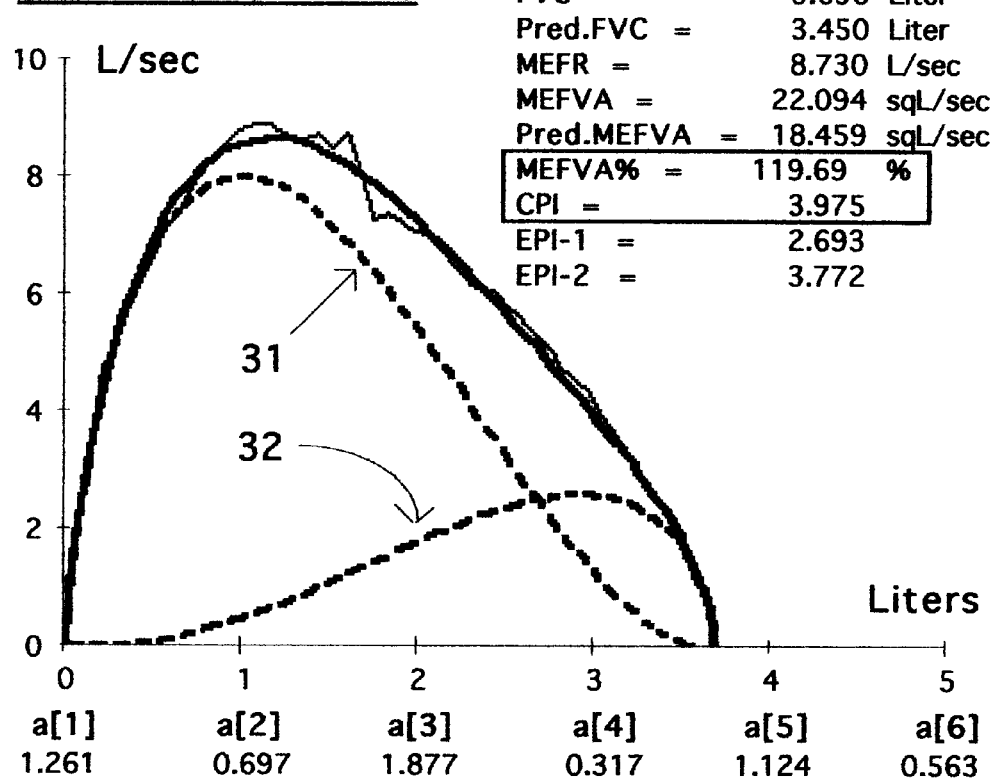
FIG. 5 is an example of the flow-volume curve of one of the subjects (thin line) with the plotted merit function (thick line) fitting on top of the first curve.

The menu item "Curve Fitting" from the menu "Merit Function" (30) of the program "MacLung©" uses the Marquardt procedure, published in "Numerical Recipes in Pascal" (Publication 2). The merit function of the flow-volume curve for lung mechanics, with the coefficients and exponents is:

$$\text{Flow}=a_1,V^{a}2,(FVC-V)^{a}{}_3+a_r,V^{a}{}_5, (FVC-V)^{a}{}_6,$$

where
V or Volume is the variable volume measured with the spirometer in liters,
FVC is the maximum volume at the abscissa crossing,
$a_1$ and $a_4$ are the coefficients of the two building curves as shown in FIG. 5 ($a_1>a_4$),
$a_2$ and $a_3$ are the exponents from the first building curve (31) where $a_3>a_2$,
$a_5$ and $a_6$ are the exponents from the second building curve (32) where $a_5>a_6$.

With these six calculated parameters it is possible to observe whether the plotted merit function's curve fits over the existing patient curve or not. Sometimes the curve made with the supposed merit function does not fit. If this happens, another set of seed values for the iterative calculations solves the parameters for the higher degree polynomial. To judge what the new seed values should be the program gives the option of to changing the parameters at will. The menu item "Save Parameters" upon user request shows the parameters in six fields, before saving. Their values cab be modified as required and then saved in a file. The new curve can be examined after each modification. When near fitting is achieved the values should become the new seeds and then a re-calculation initiated by the menu item "New Seeds" should result in a good fit. The seed searching method could be automated.

With the menu item "New Indices" the program integrates the MEFVA in square liters per second and uses a related procedure to differentiate the MEFR value from the merit function. The menu item also delivers the proportionality indices CPI, EPI-1 and EPI-2 in undimentional numbers as outlined before.

A more detailed description of the methods that led to the invention, calculations and computer program about the invention can be found in the chapteres 4 and 5 from the trilogy "Smoky Fires."

I claim:

1. A spirometer with a volume sensor, flow sensor or sound generator that form an analog electrical signal converted to a stream of digital values calculates the area under and parameters of a merit function of a flow-volume curve generated by a breathing, wherein the merit function is calculated as follows: flow=$a_1.V^a2. (FVC-V)^a3+a_4.V^a5.(FVC-V)^a6$, wherein coefficients $a_1$ and $a_4$ respectively are in a first and second building function, a power to which volume $a_2$ and $a_3$, and volume difference FVC-V, $a_3$ and $a_6$, should be raised in a flow merit function from a flow-volume curve for lung mechanics in solving the many equations generated by inserting calculated volume and flow values at digital sampling times, during a breathing exercise or flow of any particle, gas or fluid, into the merit function until a best fit curve is established for the merit function.

2. The spirometer of claim 1, wherein for comparative reasons volume and flow lung indices can be calculated and displayed graphically with their association radiant and point connecting lines.

3. The spirometer of claim 2, wherein from the calculated volume and flow values at the intervals of digital sampling time during a breathing exercise the area under a flow-volume curve expressed in square liters per second, which in case of a forced breathing exercise is a maximum expiratory flow-volume area is calculated either with the formula $$ABS[\{(x_1{}^1 x_2).(y_1-y_2)^1(x_2+x_3).(y_2-y_3)+\ldots+(X_n+X_{n+1}).(Y_n-Y_{n+1})\}/2],$$

or as an integral from a merit function of the flow-volume curve between zero and the maximum volume for that exercise or any other particle, gas or liquid flow.

* * * * *